(12) United States Patent
Chambers et al.

(10) Patent No.: US 6,387,857 B2
(45) Date of Patent: *May 14, 2002

(54) PERSONAL CLEANSING COMPOSITIONS CONTAINING HIGH LEVELS OF HUMECTANTS

(75) Inventors: John George Chambers; Phillip Moore, both of Wirral (GB)

(73) Assignee: Unilever Home & Personal Care USA, division of Conopco, Inc., Greenwich, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/504,189

(22) Filed: Feb. 15, 2000

(30) Foreign Application Priority Data

Feb. 17, 1999 (GB) ................................ 9903639

(51) Int. Cl.[7] .............................. C11D 1/02; C11D 1/94; C11D 3/44
(52) U.S. Cl. ................ 510/135; 510/119; 510/125; 510/127; 510/130; 510/136; 510/137; 510/156; 510/159; 510/371; 510/407; 510/414; 510/426; 510/432
(58) Field of Search ................... 510/119, 125, 510/127, 130, 135, 136, 137, 156, 159, 371, 407, 414, 426, 432

(56) References Cited

U.S. PATENT DOCUMENTS 5,234,619 A * 8/1993 Greene et al. .............. 252/108
5,716,919 A * 2/1998 Sano ......................... 510/159

FOREIGN PATENT DOCUMENTS

| FR | 2694569 | * | 2/1994 |
| WO | 97/38672 | * | 10/1997 |

OTHER PUBLICATIONS

International Search Report Application No. PCT/EP00/01188 mailed Apr. 27, 2000.

* cited by examiner

*Primary Examiner*—Charles Boyer
(74) *Attorney, Agent, or Firm*—Ronald A. Koatz

(57) ABSTRACT

A personal wash liquid composition which comprises 10 to 40% of one or more anionic surfactants, 30 to 50% of one or more humectants, and less than 55% water, characterized in that the water activity of the product is less than 0.9. Compositions according to the invention have been found to have self-preserving properties.

3 Claims, No Drawings

PERSONAL CLEANSING COMPOSITIONS CONTAINING HIGH LEVELS OF HUMECTANTS

This invention relates to liquid cleansing compositions, in particular liquid cleansing products which are high foaming and have a high degree of mildness.

In recent years, it has increasingly become a desirable attribute of commercially available cleansing products, in particular those products for personal washing, that such products combine a rapid and abundant lather with improved mildness, in order to minimise skin damage.

It is well known that anionic surfactants confer lathering properties to compositions in which they are contained. A previously used approach to improving the mildness of compositions containing anionic surfactants has been to partially replace the anionic surfactants with a suitable coactive surfactant, which is typically an amphoteric and/or a nonionic surfactant. Without being bound by theory, it is thought that this partial replacement of the anionic surfactant in the composition serves to reduce the critical micellar concentration of the anionic surfactant composition, and thereby reduce its harshness.

A further approach to ameliorating the harshness of anionic surfactant containing compositions has been to include in the composition one or more hydrophobic and emollient materials, such as for example silicone oils, mineral oils or cholesterol. The addition of such hydrophobic materials has generally proved successful in enhancing the mildness of the cleansing composition, but with a tendency to consequently reduce the amount of lather that they produce in use, because of their hydrophobic nature.

In addition, a farther problem encountered is that cleansing compositions general have a tendency to be susceptible to bacterial and microbial gradation; this is unacceptable for any product which is to be applied to e skin for the purposes of washing or cleansing. Hence, with such products, usually a necessary component of the composition is a suitable organic anti-bacterial and/or anti-microbial agent. Typical examples of anti-microbial and/or anti-bacterial agents which are commercially available include those under the trade names Kathon CG (ex Rohm & Hass), Phenoxyethanol (ex Nipa Laboratories), Parabens (ex Nipa laboratories), Germall 11 (ex ISP) and Glydant plus (ex Lonza), as well as materials such as formaldehyde.

However, a disadvantage of incorporating such organic anti-bacterial and/or anti-microbial compositions into a personal wash composition is that these materials can provoke adverse skin reactions. This is thought to be due to their mode of action, and therefore their levels in the commercial product must be minimised. In addition, a number of anti-bacterial and/or anti-microbial agents are suspected of toxicity.

It would therefore be highly advantageous to manufacture a personal wash composition which has good lathering properties and enhanced mildness, whilst at the same time is devoid of any recognised organic anti-bacterial and/or anti-microbial agents, but which nevertheless possessed anti-microbial and/or antibacterial properties.

We have surprisingly found that it is possible to provide liquid personal wash compositions which have high levels of lather generation and very good levels of mildness, but which are absent any recognised organic anti-microbial and/or anti-bacterial agents. Thus, according to a first aspect of the invention, there is provided a personal wash liquid composition which comprises 10 to 40% of one or more anionic surfactants, 30 to 50% of one or more humectants, and less than 55% water, characterised in that the water activity of the product is less than 0.9.

Conveniently, compositions according to the invention are free of any anti-microbial and/or anti-bacterial agents.

Compositions according to the invention preferably contain at least 10% water. Compositions are also ideally not encapsulated.

Compositions according to the invention comprise relatively high levels of humectants, which preferably are polyol humectants. Examples of suitable humectants include glycerol, sorbitol, polyethylene glycol, and mono- and oligomeric sugars. A particularly preferred humectant is glycerol. Although not wishing to be bound by theory, it is believed that compositions according to the invention can exist satisfactorily without the use of conventional anti-microbial and/or anti-bacterial agents, because of the relatively low maximum water activity of the compositions. In particular, an upper level of water activity of 0.9 has been found, at which level or below cosmetic compositions according to the invention are "self preserving".

In the context of the invention, the "water activity" (a) of the composition is defined as $a=p/p_o$, where p is the measured partial pressure of the solution and $p_o$ is the partial pressure of distilled deionised water. Unless stated otherwise, all water activities are quoted are at ambient temperature. Further references to water activity (or relative humidity, where relative humidity (RH)=100 a) can be found in Morris, C. and Leech, R., "Natural and Physical Preservative Systems", Curry, J. "Water Activities and Preservatives", Cosmet. Toilet. 100, 53–55, and Christian, J. H. B., "Reduced Water Activity". In:Silliker, J. H. (ed) "Microbial ecology of Foods", vol. 1, Academic Press, New York, pp170–192.

In addition to the relatively low water activity that the high levels of humectants provide in topical compositions, we have surprisingly found that relatively high levels of humectants do not negatively affect the lathering or sensorial properties of the topical compositions. They can however contribute positively to the mildness of the product.

Compositions according to the invention have a water activity of less than 0.9, preferably less than 0.87, more preferably less than 0.85, and even more preferably less than 0.81.

Cosmetic compositions according to the invention comprise a surfactant component which itself contains an anionic surfactant. The surfactant component contained in the composition may be any combination of surfactants, provided that it comprises an anionic surfactant, and that it provides the composition with a suitable level of foaming. As such, the surfactant component of the composition may comprise in addition to anionic surfactants soaps, cationic, nonionic, zwitterionic and amphoteric surfactants, and mixtures thereof.

Suitable soaps include these having carbon chain lengths of $C_8$–$C_{24}$, be saturated or unsaturated, and have any appropriate cation, such as sodium, potassium, ammonium or triethylammonium.

The composition according to the invention comprises an anionic surfactant, which may preferably be chosen from alkyl sulphates, alkyl ether sulphates, alkyl sulphonates, alkyl aryl sulphonates, olefin sulphonates, acyl sarcosinates, acyl taurides, acyl isethionates, nonoalkyl sulphosuccinates, dialkylsulphosuccinates, N-acylated α-amino acids, alkyl carboxylates, monoalkyl phosphates and dialkyl phosphates, and mixtures thereof. Specific examples of suitable anionic surfactants include:

alkyl sulphates, such as sodium lauryl sulphate [eg EMPICOL CX available from Albright and Wilson], and triethanolaminde lauryl sulphate [eg EMPICOL TL40/T, available from Albright and Wilson];

alkylether sulphates, such as sodium lauryl ether sulphate [eg EMPICOL ESB70, available from Albright and Wilson];

alkyl sulphonates, such as sodium alkane ($C_{13-18}$) sulphonate [eg HOSTAPUR SAS 30, available from Hoechst];

alkylaryl sulphonates, such as sodium alkyl benzene sulphonate [eg TEEPOL CM44, available from Shell];

olefin sulphonates, such as sodium olefin sulphonate ($C_{5-18}$) [eg HOSTAPUR OS, available from Hoechst];

acyl sarcosinates, having the structure: (51)

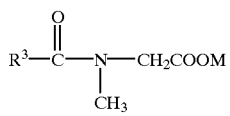

where $R^3$ is chosen from $C_{6-14}$ alkyl, and

M is a counterion chosen from alkali metals, ammonium and substituted ammonium such as alkanolammonium.

An example of an acyl sarcosinate having the structure (51), is sodium lauryl sarcosinate [eg HAMPSOYL L-95, available from Grace].

acyl taurides, having the structure (52):

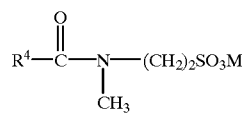

wherein $R^4$ is chosen from $C_{8-18}$ alkyl;

An example of an acyl tauride having the structure (52) is coconut methyl taurine [eg FENOPEN TC 42, available from International Specialty Products].

acyl isethionates, having the structure (53):

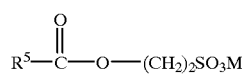

wherein $R^5$ is chosen from $C_{8-18}$ alkyl;

An example of an acyl isethionate having the structure (53) is sodium acyl isethionate [eg JORDAPON Cl, available from Jordon].

monoalkyl sulphosuccinates, having the structure (54):

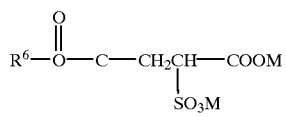

where $R^6$ is chosen from $C_{10-20}$ alkyl.

Examples of monoalkyl sulphosuccinates having the structure (54) include:

sodium lauryl sulphosuccinate [eg EMPICOL SLL, available from Albright and Wilson];

magnesium alkyl sulphosuccinate [eg ELFANOL 616 Mg, available from Akzo];

sodium lauryl ethoxysulphosuccinate [eg EMPICOL SDD, available from Albright and Wilson];

coconut monoethanolamide ethoxysulphosuccinate [eg EMPICOL SGG];

disodium lauryl polyglycolether sulphosuccinate [eg SURTAGENE S30, available from CHEM-Y];

polyethyleneglycol sulphosuccinate [eg REWOPOL SBFA 30, available from REWO];

dialkyl sulphosuccinates, having the structure (55):

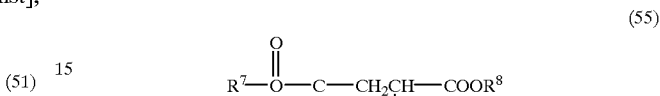

where $R^7$ and $R^8$ are the same or different, and are chosen from $C_{6-14}$ alkyl.

An example of a dialkyl sulphosucciante having the structure (55) is sodium dilauryl sulphosuccinate [eg EMCOL 4500, available from Witco];

N-acylated amino acids, such as sodium lauroyl glutamate [eg AMISOFT LS-11 (F), available from Ajinomoto Co Inc], potassium cocoglutamate [e.g. AMISOFT CK11, available from Ajinomoto Co Inc], potassium cocoglycinate [e.g. AMILITE GCK 11F] and potassium cocosarcosinate.

alkyl ether carboxylates, such as $C_{12-14}O(EO)_4OCH_2CO_2Na$ [eg AKYPO RLM 38, available from Akzo];

monoalkyl phospates and dialkyl phospates, such as dioctyl phosphate;

Further examples of anionic surfactants (and of the other types of surfactants) are described in "Surface Active Agents and Detergents" (vols. I and II), by Schwartz, Ferry and Bergh. Preferred anionic surfactants include aminocarboxylate surfactants.

In certain embodiments, preferred anionic surfactants include alkyl ether sulphates, fatty acid soaps, alkyl sulphates, alkyl sulponates, isethionic acid derivatives, and mixtures thereof. In certain embodiments, preferred non-soap anionic surfactants may be $C_8$–$C_{22}$ alkyl unsubstituted isethionates.

The composition of the invention can also comprise an amphoteric surfactant. Suitable amphoteric surfactants are derivatives of aliphatic quaternary ammonium, phosphonium and sulphonium compounds, wherein the aliphatic radicals contain from 8 to 18 carbon atoms, and may be straight chain or branched, and further contain an anionic water solubilising group, such as carboxyl, sulphonate, sulphate, phosphate or phosphonate.

Preferred amphoteric surfactants include:

Alkyl betaines, having the structure (58):

where $R^1$ is $C_{1-16}$ alkyl.

An example of an alkyl betaine having the structure (58) is lauryldimethyl betaine [eg EMPIGEN BB, available from Albright and Wilson].

alkylamidopropyl betaines, having the structure (59):

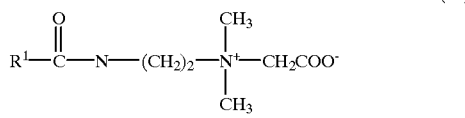
(59)

An example of an alkylamidopropyl betaine having the structure (59) is cocamidopropyl betaine (eg TEGOBETAIN L7, available from Goldschmidt);

alkylamphoglycinates or Alkylamphopropionates having the structure (60):

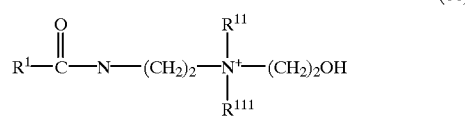
(60)

where $R^{11}$ is chosen from H, $CH_2COO^-$ and $(CH_2)_2COO^-$, and $R^{111}$ is chosen from $CH_2COO^-$ and $(CH_2)_2COO^-$.

Suitable examples of compounds (60) are cocoamphoglycinate (available from International Specialty Products), and cocoamphopropionate;

sultaines, having the structure (61):

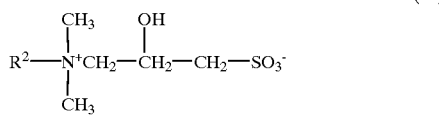
(61)

where $R^2$ is chosen from $C_{12-16}$ alkyl alkylamido groups.

An example of a sultaine having the structure (61) is cocamidopropylhydroxysultaine [eg CYCLOTERIC BET-CS, available from Alcolac).

A further suitable amphoteric surfactant is a cocamidopropyl trimethyl ammonium chloride, such as Empigen CSC, available from Albright and Wilson.

The most preferred amphoteric surfactants are lauryl dimethyl betaine and cocamidopropyl betaine. Such amphoteric surfactants can contribute to the foaming of the skin cleansing composition, while ameliorating the harshness of the anionic surfactant.

The composition of the invention can also comprise a nonionic surfactant. Suitable nonionic surfactants include polyoxyethylene alkyl esters, polyoxyethylene alkyl ethers, and alkyl polyglycosides.

A suitable example of a polyoxyethylene alkyl esters is that having the CTFA designation Polysorbate 80 which is a mixture of oleate esters of sorbitol and sorbitol anhydrides, condensed with approximately 20 moles of ethylene oxide. Also suitable is Polysorbate 20 which is a mixture of laurate esters or sorbitol and sorbitol anhydrides condensed with approximately 20 moles of ethylene oxide.

Polysorbate 80 and Polysorbate 20 are available commercially as TWEEN 80 and TWEEN 20 respectively, from ICI Americas.

Also suitable for use in the compositions of the invention is the polyethylene glycol ether of $C_{9-11}$ alcohol with an average of 8 ethoxy units, which is available commercially as NONIDET LE-8T or as SYNPERIONIC 91-8T, and the polyethylene glycol ether of $C_{12-15}$ alcohol with an average of 9 ethoxy units which is available commercially as DOBANOL 25-9.

Particularly useful alkyl polyglycosides include the glycosides of glucose or glucose oligomers where the alkyl chain can be $C_{8-16}$ and the average number of glucose units is 1 to 2. A suitable example is ORAMIX NS 10, which is the glucoside of $C_{10-12}$ fatty alcohol with an average of about 1.5 glucose units.

Conveniently, the total level of surfactant present in the composition is a level of 10–50% by weight. Preferably the total level of surfactant in the composition is at least 12% by weight; preferably, the level of surfactant in the composition is less than 35% by weight. The anionic component of the surfactant content of the composition can typically be 40–100% of the total surfactant content of the composition.

Preferably, the ratio of anionic surfactants to co-surfactants (ie amphoteric and/or nonionic surfactant) is greater than or equal to 1:1.

The invention will now be further described by way of example only.

EXAMPLE

Examples 1–3 were prepared by the simple addition with stirring of the components of the composition to each other, and contain combinations of a simple anionic surfactant and one or both of glycerol and polyethylene glycol, (MWt= 4000) as the humectants, at total levels of 30–50% by weight of product. The measured water activities of these products are shown, and are all less than 0.9. Example 4 contains an anionic/amphoteric (betaine) surfactant system with a high level of glycerol, and also exhibits a water activity of less than 0.9. All of these compositions were found to be self-preserving.

Water activity was measured by using a Novasina water activity centre fitted with enRSK/CK-4 sensors. The apparatus was calibrated using a standard range of salt solutions, and incubates samples in sealed vessels at set temperatures (in this instance 25° C.). Samples for analysis were placed into plastic cups which were put into a bowl, which in turn were clamped under the sensor for a period of 45–60 minutes. Water activity values could then be read from the apparatus.

| | Level (wt %) | | | |
|---|---|---|---|---|
| Example | 1 | 2 | 3 | 4 |
| Component | | | | |
| Sodium Lauryl Ether Sulphate | — | — | — | 12 |
| Coco amidopropyl betaine | — | — | — | 6 |
| K Coco Glycinate | 20 | 18 | 20 | — |
| Glycerol | 30 | 40 | 30 | 40 |
| PEG 4000 | 10 | 10 | — | — |
| PEG 160 sorbitan tri-stearate | — | 4 | — | — |
| TEA Caprylate | — | 4 | — | — |
| Water | | to 100% | | |
| Water activity (Aw) | 0.803 | 0.668 | 0.854 | 0.778 |

Examples 5 and 6 were similarly prepared, and contain an anionic surfactant and an anionic/amphoteric (betaine) surfactant combination, but without the high level of humectants. These two systems both have water activities exceeding 0.9, and were found to be not self-preserving.

|  | level (wt %) | |
| --- | --- | --- |
| Example | 5 | 6 |
| Potassium cocoglycinate | 10 | — |
| Sodium lauryl ether sulphate | — | 12 |
| Cocoamidopropyl betaine | 10 | 6 |
| Water | to 100 | |
| Water Activity | 0.987 | 0.987 |

Further, when examples 4 and 6 were subjected to biological challenge testing, being challenged with a mixture of Gram negative bacteria, the composition of example 4 was found to contain no surviving organisms after 24 hours and 3 days. In contrast, the composition of example 6 was found to contain high numbers of surviving bacteria after 24 hours and 3 days.

Examples 7–10 illustrate typical commercial personal wash liquids. Their water activities all exceed 0.9 and hence are not self-preserving. In order to prevent bacterial growth, these systems must contain a preservative or be suitable packaged to minimise bacterial contamination.

| Example | Product Name/Country | Water activity |
| --- | --- | --- |
| 7 | Lux Facial wash/Japan | 0.968 |
| 8 | UK Dove Shower | 0.969 |
| 9 | U.S. Dove Body Wash | 0.943 |
| 10 | German Nivia Bath Care | 0.935 |

Examples 11–12

In order to demonstrate the effect of high level of humectant on mildness, two products were prepared and tested as follows.

An anionic/amphoteric surfactant system (SLES/CAPB, weight ratio 2:1) system was prepared at 18% total surfactant level, with and without 40% glycerol. A controlled clinical dryness test was carried out with the two products.

The assessment test used was a two week test. In the first week, the skin was dried using Knights Castille soap, with the products being tested in the second week. To produce the drying, panellists washed each forearm up to four times daily using Knights Castille soap for 45 seconds, followed by a 15 second rinse. The forearms were then assessed before the last wash each day for dryness and erythema.

In the second week, 24 panellists with dry forearms were assessed and then washed using 1 $cm^3$ of the formulated product. Panellists washed each arm with either product for a total of 45 seconds four times per day, except on the fifth day on which three washes were performed, followed by 15 second rinses, and then were patted dry. The sites were graded for erythema and dryness immediately prior to each wash, and two hours after the third wash on day 5.

Corneometer readings are made by gently resting a conductance probe on the skin surface for a few seconds prior to the start of the trial on day 1, at the start of the test in week two, and again on the last day of the test. The test provides a measure of the hydration state of the outer layer of skin.

The results clearly showed that the glycerol-containing product was significantly less drying by visual and instrumental assessment (corneometry).

What is claimed is:

1. A foaming personal wash liquid composition comprising:
   (a) 10% to 40% of one or more anionic surfactant;
   (b) a cosurfactant comprising amphoteric surfactant;
   (c) 30 to 50% of one or more humectants selected from the group consisting of glycerol, sorbitol, mono- or oligomeric sugar and mixtures thereof;
   (d) 24% to 55% water; wherein the water activity of the product is less than 0.9;
wherein said composition is free of antimicrobial and/or antibacterial agent; and wherein the ratio of anionic surfactant to cosurfactant is greater than or equal to 1:1.

2. A personal wash composition according to claim 1, wherein the composition has a water activity of less than 0.87.

3. A personal wash composition according to claim 1, wherein the composition is self-preserving.

* * * * *